(12) United States Patent
Ivorra et al.

(10) Patent No.: US 7,674,249 B2
(45) Date of Patent: Mar. 9, 2010

(54) GELS WITH PREDETERMINED CONDUCTIVITY USED IN ELECTROPORATION OF TISSUE

(75) Inventors: Antoni Ivorra, Berkeley, CA (US); Boris Rubinsky, Givataaim (IL)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/872,985

(22) Filed: Oct. 16, 2007

(65) Prior Publication Data
US 2008/0214986 A1 Sep. 4, 2008

Related U.S. Application Data

(60) Provisional application No. 60/829,587, filed on Oct. 16, 2006.

(51) Int. Cl.
*A61M 31/00* (2006.01)
(52) U.S. Cl. .................. 604/500; 604/501; 604/20
(58) Field of Classification Search .................. 604/20, 604/21, 500, 501, 506, 507, 508, 511
See application file for complete search history.

(56) References Cited

U.S. PATENT DOCUMENTS

| | | | |
|---|---|---|---|
| 1,653,819 A | 12/1927 | Northcott et al. | |
| 4,016,886 A | 4/1977 | Doss | |
| 4,226,246 A | 10/1980 | Fragnet | |
| 4,262,672 A | 4/1981 | Kief | |
| 4,407,943 A | 10/1983 | Cole et al. | |
| 4,810,963 A | 3/1989 | Blake-Coleman et al. | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |
| 5,098,843 A | 3/1992 | Calvin | |
| 5,134,070 A | 7/1992 | Casnig | |
| 5,173,158 A | 12/1992 | Schmukler | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |

(Continued)

FOREIGN PATENT DOCUMENTS

DE 863111 1/1953

(Continued)

OTHER PUBLICATIONS

Davalos et al., "Tissue Ablation with Irreversible Electroporation" Annals of Biomedical Engineering, 33(2):223-231 (Feb. 2005).

(Continued)

*Primary Examiner*—Kevin C Sirmons
*Assistant Examiner*—Bhisma Mehta
(74) *Attorney, Agent, or Firm*—Karl Bozicevic; Bozicevic, Field & Francis LLP

(57) ABSTRACT

Gel compositions with adjusted conductivity are disclosed which compositions are used for directing reversible electroporation and irreversible electroporation of cells and tissue. The gel compositions are also used in a similar manner in order to carry out thermotherapy on cells and tissues.

22 Claims, 11 Drawing Sheets

U.S. PATENT DOCUMENTS

| | | |
|---|---|---|
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann et al. |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,865,787 A * | 2/1999 | Shapland et al. ............... 604/21 |
| 5,873,849 A | 2/1999 | Bernard |
| 5,919,142 A | 7/1999 | Boone et al. |
| 5,944,710 A * | 8/1999 | Dev et al. .................... 604/500 |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Hofmann et al. |
| 6,085,115 A | 7/2000 | Weaver et al. |
| 6,090,016 A | 7/2000 | Kuo |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky et al. |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,670 B2 | 2/2004 | Chomenky et al. |
| 6,702,808 B1 | 3/2004 | Kreindel |
| 6,795,728 B2 | 9/2004 | Chomenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 2001/0044596 A1 | 11/2001 | Jaafar |
| 2002/0010491 A1 | 1/2002 | Schoenbach et al. |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088199 A1 | 5/2003 | Kawaji |
| 2003/0130711 A1 | 7/2003 | Pearson et al. |
| 2003/0170898 A1 | 9/2003 | Gundersen et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0243107 A1 | 12/2004 | Macoviak |
| 2004/0267189 A1 | 12/2004 | Mavor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 * | 12/2005 | Deem et al. .................... 607/42 |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0043345 A1 | 2/2007 | Davalos et al. |
| 2007/0118069 A1 | 5/2007 | Persson et al. |
| 2008/0052786 A1 | 2/2008 | Lin et al. |

FOREIGN PATENT DOCUMENTS

| | | |
|---|---|---|
| DE | 4000893 | 7/1991 |
| EP | 0378132 | 7/1990 |
| WO | 9639531 | 12/1996 |
| WO | 0020554 | 4/2000 |
| WO | 0107584 | 2/2001 |
| WO | 0107585 | 2/2001 |
| WO | WO 01/07583 | 2/2001 |
| WO | 0181533 | 11/2001 |
| WO | 2004037341 | 5/2004 |

OTHER PUBLICATIONS

Dean, D.A., "Nonviral gene transfer to skeletal, smooth, and cardiac muscle in living animals" Am. J. Physiol. Cell Physiol., 289:233-235 (2005).

Gehl et al., "In vivo electroporation of skeletal muscle: threshold, efficacy and relation to electric field distribution" Biochimica et Biophysica Acta, 1428:233-240 (1999).

Gothelf et al., "Electrochemotherapy: results of cancer treatment using enhanced delivery of bleomycin by electroporation" Cancer Treatment Reviews, 29:371-387 (2003).
Miklavcic et al., "The Importance of Electric Field Distribution for Effective in Vivo Electroporation of Tissues" Biophysical Journal, 74:2152-2158 (May 1998).
Miklavcic et al., "A validated model of in vivo electric field distribution in tissues for electrochemotherapy and for DNA electrotransfer for gene therapy" Biochimica et Biophysica Acta, 1523:73-73 (2000).
Neumann et al., "Gene transfer into mouse lyoma cells by electroporation in high electric fields" The EMBO Journal, 1(7)841-845 (1982).
Amasha et al., Clin Phys. Physiol Meas, 9:49-53 (1988).
Andreason (1993) J. Tiss. Cult. Meth. 15:56-62.
Barber (1993) Advances in Biomedical Engineering, pp. 165-173.
Beneken and Thevenia (eds) IOS Press pp. 165-173 (1993).
Blad et al., Physiol Meas., 17:A105-A115 (1996).
Brown et al., Clin Phys Physiol Meas, 13:175-179 (1992).
Cook et al. (Aug. 1994) IEEE Transactions on Biomedical Engineering, 41(6):713-722.
Crowly, Biophysical Journal, 13:711-724 (1973).
Davalos et al., IEEE Transactions on Biomedical Engineering, 49(4):400-403 (Apr. 2002).
Dev et al., IEEE Transactions of Plasma Science, 28(1):206-223 (Feb. 2000).
Duraiswami et al., (1998) Engineering and Analysis with Boundary Elements, 22:13-31.
Duraiswami et al. (1997) Chemical Engineering Science, 32(13:2185-2196.
Duraiswami et al. (1997) Boundary Element Technology XII, pp. 226-237.
Erez et al., J. Biomech. Eng., 102(1):42-9 (1980).
Fox et al. (May 1997), Sampling Conductivity Images Via MCMC, Mathematics Department, Auckland University, New Zealand.
Gencer et al. (Feb. 1996) Transactions on Biomedical Engineering, 43(2):139-149.
Gilbert et al. (1997), Biochimica et Biophysica Act, 1334:9-14.
Griffiths et al. (Oct. 1989) Phys. Med. Biol., 34(10):1465-1476.
Griffiths et al. (1995), IEEE Transactions on Biomedical Engineering, 42:948-954.
Griffiths et al. (1987) Phys. Med. Biol., 32(11):1435-1444 (1987).
Glidewell et al., (1993) Biomed Sci Instrum, 29:251-257.
Gumerov et al. (Jun. 1999) 13th International Conference on Boundary Element Technology, BETECH, Las Vegas Nevada.
Hapala (1997) Critical Reviews in Biotechnology, 17:105-122.
Heller et al. (1999) Advanced Drug Delivery Reviews, 35:119-129.
Ho et al. (1996) Critical Reviews in Biotechnology 16:349-362.
Holder et al. (1997) Proceedings of the X. International Conference on Electrical Bioimpedance, pp. 512-519.
Hughes et al. (1994) Physiol Meas, 15:A199-A209.
Ivanusa et al., Radiol Oncol., 35(2):139-147 (2001).
Jaroszeski et al. (1999) Advanced Drug Delivery Reviews 35:131-137.
Kinosita et al., PNAS, 74(5):1923-1927 (May 1977).
Liu et al. (1992) Clin Phys Physiol Meas 13(Supp. A):197-200.
Lurquin (1997) Molecular Biotechnology, 7:5-35.
Lundqvist et al. (1998) Proc Natl Acad Sci USA, 95:10356-10360.
Lynn et al., J. Gen. Physiol, 26:179-93 (1942).
Mir et al (1991) C.R. Acad Sci Paris, 313(III):613-618.
Mir et al., European Journal of Cancer, 27:68-72 (1991).
Mir et al., British Journal of Cancer, 77(12):2336-2342 (1998).
Narayan et al. (1992) J. Urol., 148:1600-1604.
Neumann et al., J. Membrane Biol., 10:279-290 (1972).
Okino et al., Japanese Journal of Cancer Resesarch, 78(12):1319-21 (1987).
Schmuckler (1994) Engineering in Medicine and Biology Society, Engineering Advances: New Opportunities for Biomedical Engineers, Proceedings of the 16th Annual Internal Conference of the IEEE, vol. 1, p. A74.
Sersa et al., Br. J. Cancer, 87(9):1047-54 (2002).
Sersa et al., Oncol., 37(1):43-8 (2003).
Sharma et al (1996) Biophysical Journal, vol. 71:3229-3241.
Weaver (1993) Journal of Cellular Biochemistry, 51:426-435.
Zimmerman et al., Biophysical Journal, 14(11):881-889 (1974).
Baker, et al., Calcium-Dependent Exocytosis in Bovine Adrenal Medullary Cells with Leaky Plasma Membranes, *Nature*, vol. 276, pp. 620-622, 1978.
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1, pp. 3-22.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001, p. 1210.
Coates, C.W.,et al., "The Electrical Discharge of the Electric Eel, Electrophorous Electricus," Zoologica, 1937, 22(1), pp. 1-32.
Cowley, Good News for Boomers, *Newsweek*, Dec. 30, 1996/Jan. 6, 1997, p. 1.
Cox, et al., Surgical Treatment of Atrial Fibrillation: A Review, *Europace* (2004) 5, S20-S-29.
Davalos, et al., Theoretical Analysis of the Thermal Effects During In Vivo Tissue Electroporation, Bioelectrochemistry, vol. 61, pp. 99-107, 2003.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, pp. 1-237.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.
Edd, J., et al., In-Vivo Results of a New Focal Tissue Ablation Technique: Irreversible Electroporaton, *IEEE Trans. Biomed. Eng.* 53 (2006) p. 1409-1415.
Gauger, et al., A Study of Dielectric Membrane Breakdown in the Fucus Egg, *J. Membrane Biol.*, vol. 48, No. 3, pp. 249-264, 1979.
Gilbert, et al., the Use of Ultrasound Imaging for Monitoring Cryosurgery, Proceedings 6th Annual Conference, IEEE Engineering in Medicine and Biology, 107-111, 1984.
Huang, et al., Micro-Electroporation: Improving the Efficiency and Understanding of Electrical Permeabilization of Cells, Biomedical Microdevices, vol. 2, pp. 145-150, 1999.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998, pp. 1-16.
Miller, L., et al., Cancer cells ablation with irreversible electroporation, *Technology in Cancer Research and Treatment* 4 (2005) 699-706.
Mir, Therapeutic Perspectives of in Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Naslund, Michael J., Transurethral Needle Ablation of the Prostate, *Urology*, vol. 50, No. 2, Aug. 1997, pp. 167-172.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001, p. 1213.
Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001, p. 1204.

* cited by examiner

Figure 6
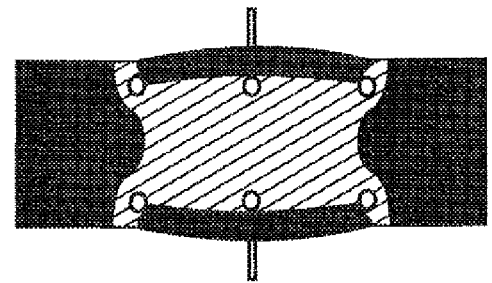
B)
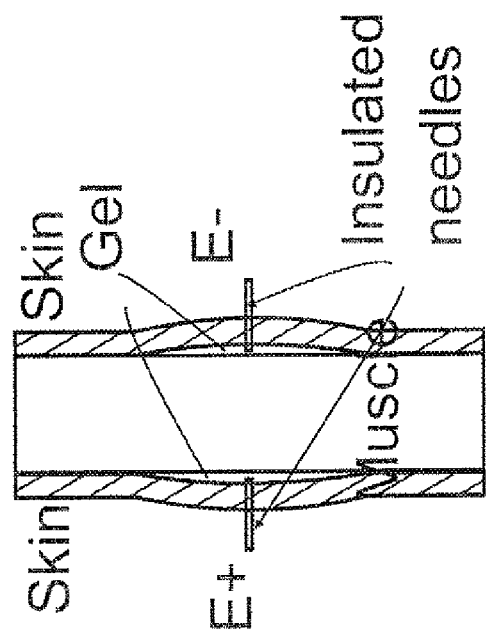
A)

GELS WITH PREDETERMINED CONDUCTIVITY USED IN ELECTROPORATION OF TISSUE

CROSS-REFERENCE

This application claims the benefit of U.S. Provisional Application No. 60/829,587 filed Oct. 16, 2006, which application is incorporated herein by reference.

GOVERNMENT RIGHTS

This invention was made with government support under federal grant nos. RR018961 awarded by National Institutes of Health. The United States Government has certain rights in this invention.

FIELD OF THE INVENTION

The invention relates generally to gels and procedures carried out with gels and more specifically to gels with specifically adjusted conductivity used in the performance of irreversible electroporation and thermotherapy of tissue.

BACKGROUND OF THE INVENTION

Electroporation, or electropermeabilization, is the phenomenon in which cell membrane permeability to ions and macromolecules is increased by exposing the cell to short (microsecond to millisecond) high voltage electric field pulses (E. Neumann, M. Schaeffer-Ridder, Y. Wang, P. H. Hofschneider, Gene transfer into mouse lymphoma cells by electroporation in high electric fields, EMBO J 1 (1982) 841-845.). Experiments show that the application of electrical pulses can have several different effects on the cell membrane, as a function of various pulse parameters; such as amplitude, length, shape, number of repeats and intervals between pulses. As a function of these parameters, the application of the electrical pulse can have no effect, can have a transient permeabilization effect known as reversible electroporation or can cause permanent permeabilization known as irreversible electroporation. Both, reversible and irreversible electroporation have important application in biotechnology and medicine.

Reversible electroporation is now commonly used with micro-organisms and cells in culture for transfection and introduction or removal of macromolecules from individual cells. Irreversible electroporation is used for sterilization of liquid media from micro-organisms. During the last decade reversible electroporation has started to be used in living tissues for in vivo gene therapy (electrogenetherapy) (M. J. Jaroszeski, R. Heller, R. Gilbert, Electrochemotherapy, electrogenetherapy, and transdermal drug delivery: electrically mediated delivery of molecules to cells, Humana Press, Totowa, N.J., 2000; D. A. Dean, Nonviral gene transfer to skeletal, smooth, and cardiac muscle in living animals, Am J Physiol Cell Physiol 289 (2005) C233-245; L. M. Mir, P. H. Moller, F. Andre, J. Gehl, in Advances in Genetics, Academic Press, 2005, pp. 83-114) and to enhance the penetration of anti-cancer drugs into undesirable cells (electro-chemotherapy) (A. Gothelf, L. M. Mir, J. Gehl, Electrochemotherapy: results of cancer treatment using enhanced delivery of bleomycin by electroporation, Cancer Treat. Rev. 29 (2003) 371-387). Recently, irreversible electroporation has also found a use in tissues as a minimally invasive surgical procedure to ablate undesirable tissue without the use of adjuvant drugs (R. V. Davalos, L. M. Mir, B. Rubinsky, Tissue Ablation with Irreversible Electroporation, Ann. Biomed. Eng. 33 (2005) 223; L. Miller, J. Leor, B. Rubinsky, Cancer cells ablation with irreversible electroporation, Technology in Cancer Research and Treatment 4 (2005) 699-706; J. Edd, L. Horowitz, R. V. Davalos, L. M. Mir, B. Rubinsky, In-Vivo Results of a New Focal Tissue Ablation Technique: Irreversible Electroporation, IEEE Trans. Biomed. Eng. 53 (2006) 1409-1415).

Electroporation is a dynamic phenomenon that depends on the local transmembrane voltage at each cell membrane point. It is generally accepted that for a given pulse duration and shape, a specific transmembrane voltage threshold exists for the manifestation of the electroporation phenomenon (from 0.5V to 1V). This leads to the definition of an electric field magnitude threshold for electroporation (Eth). That is, only the cells within areas where $E \geq Eth$ are electroporated. If a second threshold (Eth_irr) is reached or surpassed, electroporation will compromise the viability of the cells, i.e., irreversible electroporation.

Precise control over the electric field that develops in tissues is important for electroporation therapies (J. Gehl, T. H. Sorensen, K. Nielsen, P. Raskmark, S. L. Nielsen, T. Skovsgaard, L. M. Mir, In vivo electroporation of skeletal muscle: threshold, efficacy and relation to electric field distribution, Biochimica et Biophysica Acta 1428 (1999) 233-240; D. Miklavcic, D. Semrov, H. Mekid, L. M. Mir, A validated model of in vivo electric field distribution in tissues for electrochemotherapy and for DNA electrotransfer for gene therapy, Biochimica et Biophysica Acta 1523 (2000) 73-83; D. Miklavcic, K. Beravs, D. Semrov, M. Cemazar, F. Demsar, G. Sersa, The Importance of Electric Field Distribution for Effective in vivo Electroporation of Tissues, Biophys. J. 74 (1998) 2152-2158). For instance, in reversible electroporation it is desirable to generate a homogeneous electric field ($E_{th} \leq E < E_{th\_irr}$) in the region of interest and a null electric field in the regions not to be treated. Currently, optimization of the electric field distribution during electroporation is done through design of optimal electrode setups (G. A. Hofmann, in M. J. Jaroszeski, R. Heller, R. A. Gilbert (Editors), Electrochemotherapy, electrogenetherapy and transdermal drug delivery: electrically mediated delivery of molecules to cells, Humana Press, Totowa, N.J., 2000, pp. 37-61). However, there are situations in which an electrode setup alone is not sufficient for obtaining an optimal electrical field, particularly in situations such as the electroporation of irregularly shaped tissues or when the protection of specific tissue regions is required.

SUMMARY OF THE INVENTION

A method of carrying out electroporation of tissue is disclosed which includes inserting a gel into a patient wherein the gel has a predetermined conductivity relative to surrounds tissue. Current is applied across the tissue in amounts so that cells in the tissue are subjected to irreversible electroporation. The conductivity of the gel may be adjusted sufficiently below that of the surround tissue such that the gel acts as an insulator and directs the current to flow only through specific areas of targeted tissue which are subjected to the irreversible electroporation. The gel conductivity may be adjusted so that it is substantially the same as the surrounding tissue and when current is applied a homogenous electrical field is applied and a specific area of targeted tissue is subjected to irreversible electroporation. The gel may be comprised of a liquid phase of water and a solid phase of polymer such as collagen and may further comprise a therapeutically active drug. The conductivity of the gel may be adjusted by incorporating a predetermined concentration of ions which may be derived from sodium chloride.

Electroporation, cell membrane permeabilization with short electrical field pulses, is used in tissue for in vivo gene therapy, drug therapy and minimally invasive tissue ablation. For the electroporation to be successful the electrical field distribution that develops during the application of the pulses needs to be precisely controlled.

Electrolytic and non-electrolytic additives, such as gels, are used to generate the precise electrical fields required for controlled in vivo electroporation. The invention includes a series of techniques based on that approach that overcome some of the limitations of current electroporation methods based on solid electrodes.

Finite element computer simulations are used here to illustrate various applications, such as the treatment of irregularly shaped organs and interior cavities. The feasibility of the concept was demonstrated experimentally in vivo with a rat liver subjected to irreversible electroporation.

The present invention uses additives for modulating the electric properties of the treated tissues or for modifying the geometry of tissues or electrodes as a means of optimizing the electric field during tissue electroporation. Additives include the use of fluids with various conductivities and, more specifically, the use of gels with various ionic contents. Gels are particularly interesting because they can behave as solids but they can also be injected easily with a syringe.

There are numerous uses of this concept, some of which are listed below. The invention provides a wide range of additional possible applications of the concept.

An aspect of the invention includes a gel which is adjusted in terms of its conductivity to be useful in connection with electroporation which can include reversible electroporation or irreversible electroporation.

Another aspect of the invention is a kit which is comprised of components used in carrying out any of reversible electroporation, irreversible electroporation, thermotherapy and the like which kit may include gels with their conductivity adjusted, instructions for carrying out the methods, and additives which can be included within the gel.

Yet another aspect of the invention is the use of a gel in the manufacture of a gel composition with a predetermined conductivity relative to surrounding tissue, for a tissue electroporation treatment where current is applied across tissue, in contact with the gel in an amount so that cells of the tissue are subjected to electroporation.

Another aspect is the use of the gel wherein the conductivity of the gel is sufficiently below that of the surrounding tissue such that when current is applied substantially no current flows through the gel and the current is directed to a specific targeted area of tissue to be electroporated.

Still another aspect of the invention is the use of the gel wherein the conductivity of the gel is substantially the same as that of surrounding tissue and when current is applied a homogeneous electrical field is applied and a specific area of targeted tissue has its cells electroporated.

Another aspect of the invention is use of a gel in the manufacture of a gel composition with a predetermined conductivity relative to surrounding tissue, for a tissue electroporation treatment where current is applied across tissue, in contact with the gel in an amount so that cells of the tissue are subjected to a temperature change sufficient to disrupt normal cell permeability.

These and other objects, advantages, and features of the invention will become apparent to those persons skilled in the art upon reading the details of the specific embodiments as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 5C and 5D compare a situation where the blood is replaced by a matched conductivity additive in 5D to provide a more homogenous electrical field.

FIG. 6 includes FIGS. 6A and 6B with FIG. 6A showing a conceptual cross-sectional view of a gel being placed between the skin and muscle and FIG. 6B showing the conceptual view of an electrical field generated.

FIG. 11 includes FIGS. 11A and 11B wherein 11A which is a microscopic photo showing the tip of a liver showing erythrocytes marked with arrows and FIG. 11B is another microscopic photo showing the central vein.

DETAILED DESCRIPTION OF THE INVENTION

Figure 1:
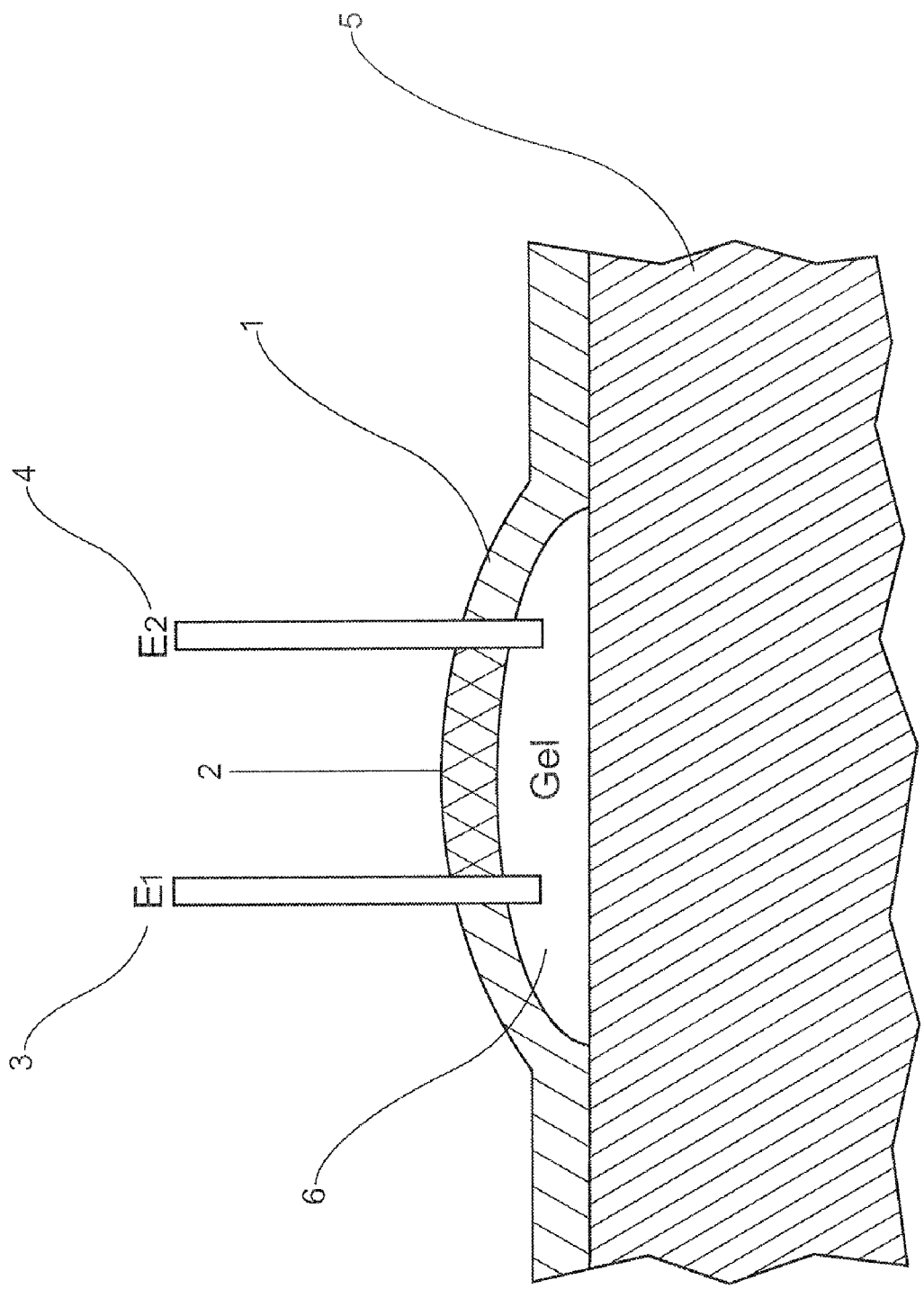
FIG. 1 is a conceptual cross sectional view showing a non-conductive gel used as an insulator below tissue to protect tissue below while allowing other tissue to be subjected to irreversible electroporation with the tissue on top positioned between two electrodes.

Before the present gels, kits and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a gel" includes a plurality of such gels and reference to "the ion" includes reference to one or more different types of ions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "gel" is used herein to refer to an apparently solid, jelly like material formed from a colloidal solution. By weight, most gels are liquid yet behave like solids. Examples include gelatin and commercially available gel materials used in connection with surgery. However, in connection with the present invention the conductivity of the gel is adjusted using different ion concentrations such as concentrations of sodium chloride in order to increase or decrease the conductivity of the gel. A typical gel includes water as the liquid phase and a polymer such as pharmaceutical grade collagen as the solid phase. Gels are considered semi-solid materials, somewhat elastic and composed of matter in a colloidal state that does not readily dissolve. In connection with the present invention the gel can be adjusted so as to provide insulation with respect to the flow of current and/or conducting heat. Gels can be modified by the inclusion of small amounts of metal particles including nano size particles (less than 1 micron in diameter or less than 0.1 micron or less than 0.01 micron in diameter) and by the inclusion of dissolved metals and ions which are dissolved into the liquid phase and become part of the colloid solution of the gel.

Conditioning of Tissue Electrical Properties or of Electrode-tissue Interfaces (1.1)

When in electroporation a current is forced to flow across different tissue layers, those with higher resistivity will be subjected to higher electric fields. Thus, some tissue layers will be more prone to electroporation than others. Although, this is not necessarily an inconvenient, it could imply that in order to reversibly electroporate some tissues it would be necessary to irreversibly electroporate others, if not to burn them because of a Joule effect. Moreover, the voltage drop at those higher resistivity layers will be significant and, in most cases, uncontrollable. Thus, in these cases it will be difficult to assess the required external voltage in order to have the sufficient electric field at the region of interest.

Furthermore, the electrode-tissue interface impedance is also inconvenient in the same sense. At the electrode surface, electron exchange reactions occur that transform electronic transport (electrode metal) into ionic transport (tissue). Such transformation also implies a resistance, and a resulting voltage drop, that will depend on different factors such as the availability of ions and their mobility.

A case that combines both phenomena is the skin-fold electroporation technique in which skin is folded and electroporated with parallel plates on opposite sides of the fold (U. Pliquett, R. Elez, A. Piiper, E. Neumann, Electroporation of subcutaneous mouse tumors by trapezium high voltage pulses, Bioelectrochemistry 62 (2004) 83-93). In most cases, skin viable tissue layers are the objective of the treatment whereas the top layer, the stratum corneum, represents an impediment to the treatment because of its high resistivity. Moreover, since the electrode-tissue interface in this case is rather dry, the availability and mobility of ions is poor and the related interface resistance is quite high. In fact, this is not only a problem for electroporation but also for different bio-electric applications involving electrodes such as external defibrillation. In these other cases, electrolytic gels and pastes have been used for decades (L. A. Geddes, Electrodes and the measurement of bioelectric events, Wiley-Interscience, New York, 1972). Therefore, it is not surprising that gels have also been adopted by researches in the electroporation field in order to improve the "contact" between the electrodes and the tissues (J. Gehl, T. H. Sorensen, K. Nielsen, P. Raskmark, S. L. Nielsen, T. Skovsgaard, L. M. Mir, In vivo electroporation of skeletal muscle: threshold, efficacy and relation to electric field distribution, Biochimica et Biophysica Acta 1428 (1999) 233-240; D. Miklavcic, K. Beravs, D. Semrov, M. Cemazar, F. Demsar, G. Sersa, The Importance of Electric Field Distribution for Effective in Vivo Electroporation of Tissues, Biophys. J. 74 (1998) 2152-2158). These compounds improve both the electrode-tissue interface impedance and the skin top layer conductivity by supplying water and ions, even in some cases they include abrasives to help to reduce the resistance of the stratum corneum layer.

Hence, conductive gels are known in the electroporation field. However, the present invention shows that in electroporation there are many additional valuable applications of electrolytic and non-electrolytic additives and gels, in addition to improving the "contact" impedance.

Insulation of Tissue Regions (1.2)

During electroporation, it is often important to ensure that certain regions of tissue are not affected by the applied electric field. One possible method to achieve this is by isolating the treated region from that to be protected with non-conductive gels, i.e. without free ions. However, it must be taken into account that: 1) once the gel is in contact with tissues, biological ions will begin to diffuse inwards and, consequently, its conductivity will increase and its behavior as insulator will be compromised after a period of time; and 2) the gel must be perfectly deposited as a continuous layer, otherwise, any cleft or hole will lead to conductive paths. Therefore, it is better to consider the use of non-conductive gels as "injectable spacers" rather than as insulation films. That is, to use them to physically separate the region to be electroporated from those to be protected.

FIG. 1 illustrates a possible application of such strategy; the top layer 1 includes an area 2, to be treated by means of irreversible electroporation with electrode 3 and 4. The area 2 represents a skin melanoma whereas the bottom region 5 represents any hypodermic tissue, such as muscle, to be protected. In this case, the gel 6 is injected hypodermically through a syringe before the application of the needle electrodes (E1 and E2). Section 3.1.2 shows the simulation results of a structure resembling this case.

Electric Field Homogenization in Irregularly Shaped Tissues (1.3)

Two parallel plate electrodes produce an almost homogeneous electric field distribution when a homogeneous tissue slab is placed in between them, as in the case of the skin-fold technique. However, as shown in section 3.1.2. (FIG. 4C), plate electrodes do not produce homogeneous electric fields when the tissue part to be treated has an irregular shape. A solution to this problem, in the spirit of using additives to modulate the electrical properties of tissue, is to fill the space between plate electrodes with a gel whose conductivity is equal or similar to that of the tissue to be electroporated ("matched conductivity gel"). By doing this, the material between the plates will become homogeneous in electrical terms and the generated electric field distribution will also be homogeneous. Computer simulations show that perfect matching between gel and tissue conductivities is not required in order to obtain very significant improvements.

Section 3.1.2. shows the simulation results of a hypothetical case related to the above. That example could represent an irregularly shaped hard tumor that needs to be reversibly electroporated through external plate electrodes.

Section 3.2 shows an in vivo experimental verification of the concept. The edge of a rat liver lobe was irreversibly electroporated between two plate electrodes. In order to homogenize the electric field, a "matched conductivity gel" was employed to fill the space between the electrodes and the liver surface.

Besides geometrical irregularities on the surface of the tissue, large blood vessels could also have a significant impact on electric field distribution. One would expect that due to their higher conductivity they may cause important field heterogeneities. In fact, we have observed treatment heterogeneities when applying electroporation through needle electrodes (not reported here) that we attribute to such phenomenon. A possible solution is the perfusion of blood vessels with fluids of similar conductivity to that of the parenchyma to be treated. Section 3.1.3. shows the simulation results of a hypothetical case in which reversible electroporation of a region that contains a blood vessel in its vicinity is performed. In this case, only a thin strip of tissue is not electroporated because of resulting field distribution heterogeneity. However, in the case of tumor ablation through electro-chemotherapy this could have dramatic consequences, particularly taking into account that the surviving tumor cells would be close to a blood vessel. Another simulation result in section 3.1.3. shows that the effect of replacing the blood with a tissue matched conductivity fluid has a positive impact.

Implementation of Injectable Electrodes (1.4)

High conductivity gels are good conductors and, therefore, they can also serve as electrodes. This implies that it is possible to implement electrodes that are soft, injectable, moldable and biodegradable, among other possible interesting features. Here we describe two possible applications of such injectable electrodes:

Shielding of Tissue Regions (1.4.1)

When voltage is applied between two electrodes, current flows through the path of least resistance, which, in most cases, coincides with the shortest path. Hence, a possible way to guarantee that a specific tissue region will be not electroporated is to place it behind the electrodes, that is, outside of the region sandwiched by the electrode pair. In some cases it will be possible to actually displace the tissues or to use spacers for separation (section 1.2.). In other cases, the strategy depicted in FIG. 2A could be employed. That is, to implement an embedded electrode in such a way that the tissue region to be protected (bottom layer in FIG. 2A) lies outside of the region between both electrodes.

Figure 2:
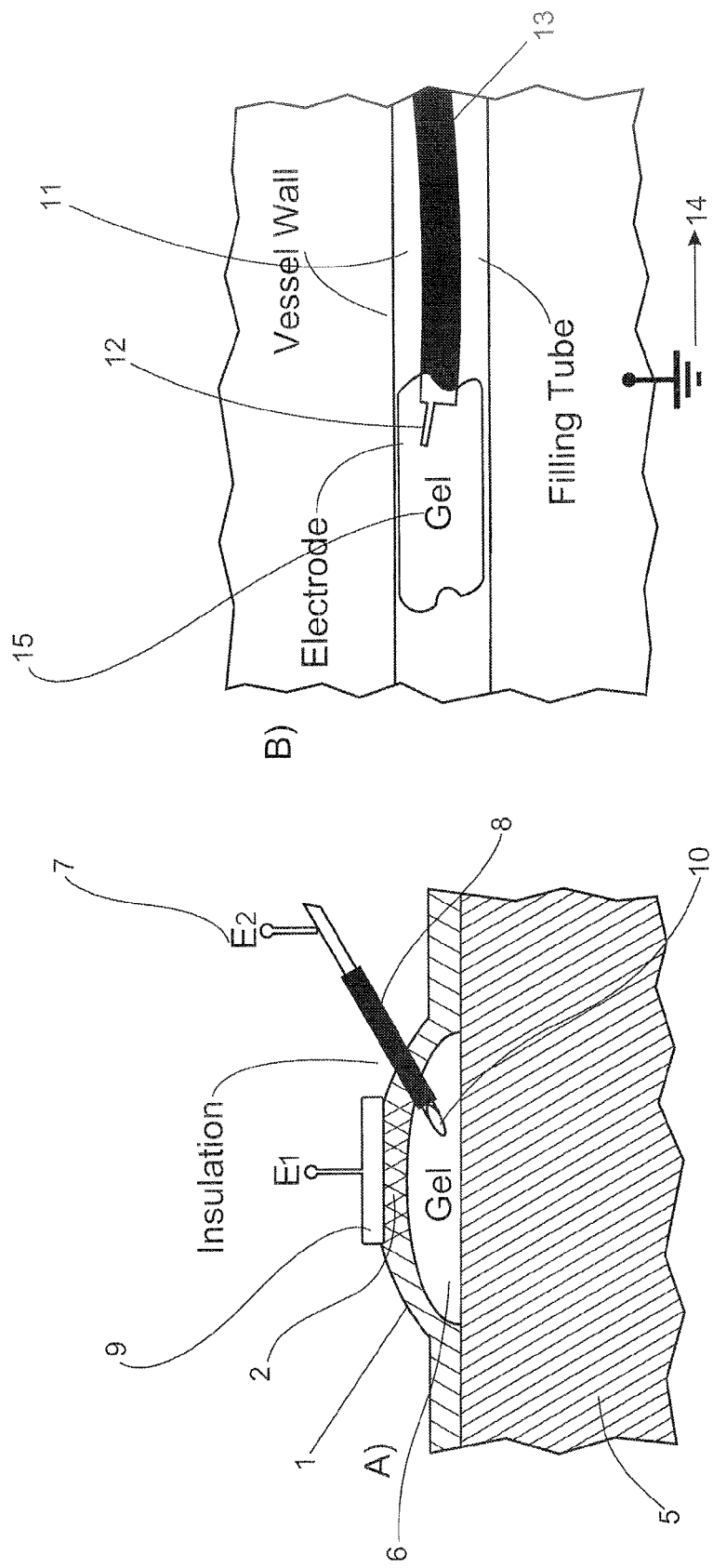
FIG. 2 includes FIG. 2A and FIG. 2B with FIG. 2A showing the gel used as an insulator to protect the tissue below and FIG. 2B showing the gel within a vessel such as a blood vessel.

The example depicted in FIG. 2A represents a case of skin 1 electroporation in which the muscle and other deeper structures 5 need to be protected. The process starts by injecting the gel 6 subcutaneously through a syringe. Then, the same injection needle 7 with an electrical insulation 8 on the shaft or a wire threaded through the skin and gel 6 is used for the electrical contact between the gel region (injected electrode) and the pulse generator terminal. In this way, roughly only the skin 2 between the gel 6 and the top electrode 9 is electroporated. An interesting feature of the proposed method is that the injectable electrodes 10 may be adapted to the morphology of the region 2 to be treated.

FIG. 2A shows using injectable an electrode 10 for protection of specific tissue regions 5. Gel 6 and electrode 10 are injected beneath the top layer. When voltage pulse is applied, only the region between the gel 6 and top electrode 9 is electroporated.

FIG. 2B shows electroporation of hollow structures such as a blood vessel 11. Gel electrode 12 is injected through a catheter 13 that is also used to connect it to the pulse generator. The opposite electrode 14 can be placed on the surface of the body.

Section 3.1.4. contains simulation results of a case which shows how injected electrodes can be employed to protect specific tissue regions. In that case, however, the objective is to reversibly electroporate the inner tissue without damaging the outer layers.

Method to Electroporate Hollow Structures (1.4.2)

Electroporation of blood vessel tissues is possible through intraluminal catheters which take advantage of the conductivity provided by blood (N. B. Dev, T. J. Preminger, G. A. Hofmann, S. B. Dev, Sustained local delivery of heparin to the rabbit arterial wall with an electroporation catheter, Catheterization and Cardiovascular Diagnosis 45 (1998) 337-345). However, in other cases, such as the gastrointestinal or urinary tracts, there is no natural electrical contact media between the intraluminal electrode and the organ walls. Flexible electrodes designed to make direct contact with walls to be treated have been proposed for these cases (D. M. Soden, J. O. Larkin, C. G. Collins, M. Tangney, S. Aarons, J. Piggott, A. Morrissey, C. Dunne, G. C. O'Sullivan, Successful application of targeted electrochemotherapy using novel flexible electrodes and low dose bleomycin to solid tumours, Cancer Letters 232 (2006) 300-310). Here we suggest that the additives investigated in this study, such as conductive gels or pastes could be a much simpler and yet effective solution. For instance, as shown in FIG. 2B, a catheter 13 could be used to inject the conductive gel 15 into a vessel 11 which when brought in contact with a wire further connected to the power supply 14 could serve as an electroporation electrode. An advantage of this strategy is that gel 15 preparation could also contain the therapeutic agent and there would be no need to entrap it with balloons or other means in the region to be treated as it is the case in intraluminal catheter for electroporation (N. B. Dev, T. J. Preminger, G. A. Hofmann, S. B. Dev, Sustained local delivery of heparin to the rabbit arterial wall with an electroporation catheter, Catheterization and Cardiovascular Diagnosis 45 (1998) 337-345).

In the example in FIG. 2B one of the electrodes 12 is the injected gel and the other 14 would be a large electrode on the surface of the body. In this way, highest electric fields will be produced around the gel 15, particularly if the vessel wall has lower conductivity than surrounding parenchyma, as it will happen in most cases. Thus, only an annular region surrounding the gel will be electroporated. Such structure is simulated in section 3.1.5.

However, it must be noted that in this case it is not trivial to compute a priori the required electroporation voltage since the impedance between the gel region and the external electrode will not be known accurately enough. In order to overcome this inconvenience the present invention measures the impedance between the internal electrode and the external electrode before the electroporation. From this measurement is obtained an approximate value of the resistance that the system during the electroporation (R). Thus:

$$J_{WALL} \approx \frac{I}{S} = \frac{\frac{V}{R}}{S} \quad (1)$$

where JWALL denotes current density at the interface between the gel and the vessel wall, I denotes the total current, V is the voltage applied by the pulse generator and S is the area of contact between the gel and the vessel (2π×radius× longitude). Then, since the Ohm's law defines the relationship between the conductivity (σ), the electric field (E) and the current density $$J = \sigma \cdot E \quad (2)$$

it is possible to obtain an expression that gives us the required voltage to obtain a specific field at the gel-vessel interface (EINTERFACE):

$$V = \sigma_{WALL} \cdot S \cdot R \cdot E_{INTERFACE} \quad (3)$$

If the vessel wall thickness is much smaller than the diameter of the vessel, then the electric field across the vessel wall will be quite uniform.

Ionic Gels

Gels are colloidal dispersions in which the dispersion medium is a liquid and the continuous medium is a solid, generally a network of polymeric chains. In the specific case that water is the liquid medium, gels are also called hydrogels. An interesting property of most gels is thixotropy, that is, they become more fluid when mechanically disturbed. Thus, whereas in steady state gels can behave like a soft solid or a high viscosity fluid, they can be injected easily through small gauge needles thanks to the effect of shear forces. Hydrogels are used extensively for various medical applications such as breast implants, wound dressings materials, drug delivery systems, electrodes and contact lenses. Hydrogels of this type can be used in connection with the present invention where characteristics such as biocompatibility, biodegradability and temperature and chemical sensitivity are achieved.

A straightforward method to generate a liquid or gel with a desired electric conductivity is by controlling the content of free ions. Presumably, hypoionic solutions will have no significant effect on living tissues if they are applied for short periods and if they are balanced with non-ionic species to achieve isotonicity. On the other hand, high conductivity gels will almost certainly imply hypertonicity. Hence, some damage to the tissue due to osmotic unbalance (cytotoxicity caused by cell dehydration) might be expected. In fact, hypertonic gels have been proposed as an ablation method (J. Rehman, J. Landman, D. Lee, R. Venkatesh, D. G. Bostwick, C. Sundaram, R. V. Clayman, Needle-Based Ablation of Renal Parenchyma Using Microwave, Cryoablation, Impedance- and Temperature-Based Monopolar and Bipolar Radiofrequency, and Liquid and Gel Chemoablation: Laboratory Studies and Review of the Literature, Journal of Endourology 18 (2004) 83-104). Nevertheless, although very highly hypertonic gels (23.4% NaCl) have been tried, the observed lesions remained small. Quite fortunately, according to the theoretical results presented here, it seems that it will not be necessary to employ concentrations above 15% NaCl (σ=240 mS/cm). Thus, taking into account that the presence of the hypertonic gels will only be required for a short period, problems regarding the biocompatibility of the materials are reduced or eliminated.

An interesting alternative to the use of ions for regulating fluid conductivity could be the use of microscopic particles, including those obtained from nanotechnology. For example, particles that combine electrical conductivity properties and magnetic properties that are manipulated through magnetic fields.

Methods (2)

Electric Field Distribution Computed by the Finite Element Method (2.1)

The present invention uses mathematical analysis to explore and illustrate the various applications of the electrolytic and non-electrolytic gels to control electroporation. To this end we employ the finite element method (FEM) to compute the electric field distribution under the assumption of constant conductivities and static currents and fields. This methodology has been used by previous researchers in the field (D. Sel, S. Mazeres, J. Teissie, D. Miklavcic, Finite-element modeling of needle electrodes in tissue from the perspective of frequent model computation, IEEE Trans. Biomed. Eng. 50 (2003) 1221; S. B. Dev, D. Dhar, W. Krassowska, Electric field of a six-needle array electrode used in drug and DNA delivery in vivo: analytical versus numerical solution, IEEE Trans. Biomed. Eng. 50 (2003) 1296; K. Sugibayashi, M. Yoshida, K. Mori, T. Watanabe, T. Hasegawa, Electric field analysis on the improved skin concentration of benzoate by electroporation, International Journal of Pharmaceutics 219 (2001) 107-112) and its validity has been proven (J. Edd, L. Horowitz, R. V. Davalos, L. M. Mir, B. Rubinsky, In-Vivo Results of a New Focal Tissue Ablation Technique: Irreversible Electroporation, IEEE Trans. Biomed. Eng. 53 (2006) 1409-1415; D. Miklavcic, D. Semrov, H. Mekid, L. M. Mir, A validated model of in vivo electric field distribution in tissues for electrochemotherapy and for DNA electrotransfer for gene therapy, Biochimica et Biophysica Acta 1523 (2000) 73-83).

The key idea of the FEM is the decomposition of an arbitrary geometry into small simple elements in which it is possible to solve the differential equations related to the phenomena under study. Given the appropriate boundary conditions, the solutions are then assembled and an approximate solution for the complete geometry is provided. With the present invention, the solved equation for each element is the Poisson's equation:

$$-\nabla \cdot (\sigma \nabla V - J^e) = Q_j \tag{4}$$

where σ is the conductivity, V is the voltage, Je is a vector denoting the externally generated current density and Qj indicates the current generated in the element (null in all the cases presented here).

The specific FEM tool used here was COMSOL Multiphysics 3.2 (www.comsol.com) and the mode chosen for the simulations was "3D conductive media DC". The boundary conditions were all insulating on the external surfaces. Unstructured meshes of tetrahedral elements were automatically generated by the FEM tool.

The geometry of the analyzed cases and other details relevant to the simulations are discussed in the next sections. Unless otherwise specified, the simulations have been performed assuming that Eth =500 V/cm (reversible electroporation threshold), $Eth_{13}irr$ =1000 V/cm (irreversible electroporation threshold), and the conductivity of the tissue (σ) is 1 mS/cm. In the resulting graphs black color indicates E<500 V/cm (no effect); hatch marks 500 V/cm≦E<1000 V/cm (reversible electroporation); and white E≧1000 V/cm (irreversible electroporation).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In Vivo Proof of Concept (2.2)

To demonstrate the feasibility of using gels for electroporation, we carried out, in addition to the mathematical analysis, an experiment in which the edge of a rat liver lobe was irreversibly electroporated between two plate electrodes.

From previous experimental studies (J. Edd, L. Horowitz, R. V. Davalos, L. M. Mir, B. Rubinsky, In-Vivo Results of a New Focal Tissue Ablation Technique: Irreversible Electroporation, IEEE Trans. Biomed. Eng. 53 (2006) 1409-1415), we know that irreversibly electroporated regions in rat liver show within 30 minutes entrapping of erythrocytes that is observable both macroscopically (darkening due to blood congestion) and microscopically. Thus, this phenomenon can be employed to assess the interface between reversible and irreversible electroporated regions and thereby distribution of electric fields during electroporation.

Experimental Procedure (2.2.1)

A male Sprague-Dawley rat (350 g) was obtained from Charles River Labs through the Office of Laboratory Animal Care at the University of California, Berkeley. It received humane care from a properly trained professional in compliance with both the Principals of Laboratory Animal Care and the Guide for the Care and Use of Laboratory Animals, prepared and formulated by the Institute of Laboratory Animal Resources and published by the U.S. National Institutes of Health (NIH).

The experiment started with anesthetization of the animal via intraperitoneal injection of Nembutal solution (50 mg/ml sodium pentobarbital, Abbott Labs, North Chicago, Ill.) for a total of 100 mg sodium pentobarbital per kg of rat. Thirty minutes later, the liver was exposed via midline incision.

After exposing the rat liver, a liver lobe was placed between two flat circular electrodes separated at a distance of 5 mm. In order to emulate a geometrical irregularity, the liver lobe edge was inserted partially between the two electrodes. The placement of the electrodes in relation to the liver resembled the illustration in FIG. 8, which at the same time is the model for the FEM simulation of the case. Then, the void space was filled with the matched conductivity gel and the electroporation pulse sequence (8 pulses of 750 V with a duration of 100 µs and a period of 100 ms) was applied by means of a commercial pulse generator (ECM 830, Harvard Apparatus; Holliston, Mass.).

Two hours and a half after the electroporation sequence, the animal was euthanized and liver samples were prepared for histological analysis.

Histology (2.2.2)

To fix the liver at its current state for microscopic viewing, we flushed the vasculature with physiological saline for ten minutes at a hydrostatic pressure of 80 mmHg from an elevated IV drip. This was accomplished by injecting the fluid into the left ventricle and letting it exit from a cut made in the right atrium. Immediately following saline perfusion, a 5% formaldehyde fixative was perfused in the same way for ten minutes. The treated liver lobe was then removed and stored in the same formaldehyde solution. Hematoxylin-eosin staining was then performed on cross-sections through the center of the treated region to study the effects of electroporation.

Gel Preparation (2.2.3)

We prepared a saline gel from a 0.045% NaCl solution, which is 20 times less concentrated than the standard physiological solution (0.9% NaCl). Such electrolyte content should produce an electrical conductivity of around 0.7 mS/cm. Reported liver conductivities maybe a little bit higher (~1 mS/cm), however, as seen in the simulations, this difference should not produce significant effects. The steps to produce the gel were: 1) add 0.8 g of raw agar to 100 ml of a 0.045% NaCl solution; 2) dissolve agar in the saline solution at boiling point; 3) cool the solution until solidification and 4) stir until gel formation.

Results and Discussion (3)

Simulation of Typical Applications (3.1)

The goal of this section is to illustrate the concepts brought in the introduction with typical examples.

Tissue Insulation (3.1.1)

Here we simulate the case discussed in FIG. 1 (section 1.2.). That is, non-conductive gel is injected underneath the top layer of tissue in order to physically separate it from bottom tissue, which needs to be protected. This particular case represents a skin melanoma that needs to be removed by irreversible electroporation.

The model used for the simulation consists of five components: 1) a square prism (20 mm×20 mm×5 mm) with conductivity=1 mS/cm that models bottom tissue (tissue 2); 2) a half ellipsoid volume (10 mm×10 mm×0.5 mm) on top of the prism with conductivity 0.1 mS/cm for the insulating gel; 3) a mantle (thickness=1 mm) with conductivity=1 mS/cm on top of both components that models top tissue (tissue 1); and 4) and 5) two cylinders (diameter=0.1 mm, length=5 mm) with high conductivity (1000 S/cm) representing the electrodes that penetrate the top mantle. The separation distance between the electrodes is 2 mm and the applied difference voltage is 1000 V. The number of elements of the mesh is 102,614.

Note that we have chosen a conductivity of 0.1 mS/cm for the insulating gel, instead of the ideal 0 mS/cm, to take account of the fact that impurities in the gel and ionic diffusion from tissue after implantation will make it not a perfect insulator.

The result of the simulation (FIG. 3) shows that, although the top tissue 2 is irreversibly electroporated throughout the entire area surrounding the electrodes 3 and 4, damage to the bottom layers is minimal and only two single spots experience reversible electroporation. It is interesting to note that the simulated gel 6 is not completely non-conductive, in fact, its conductivity is only one order of magnitude lower that the conductivity of the tissues.

Figure 3:
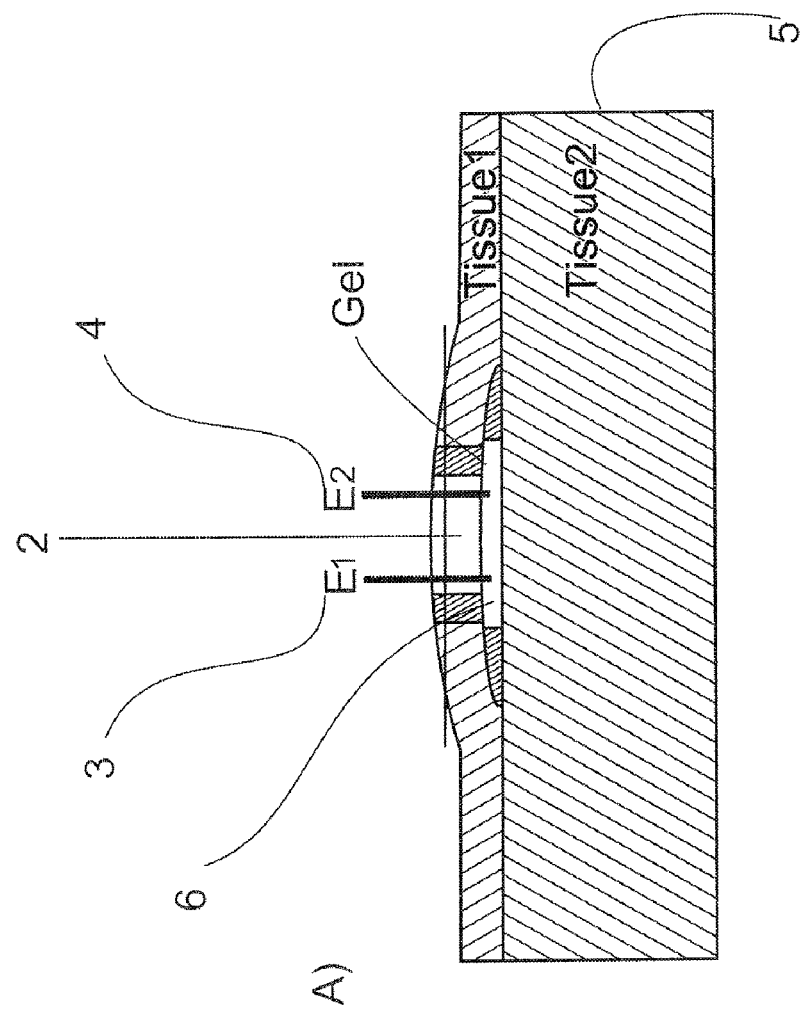
FIG. 3 includes 3A and 3B with FIG. 3A showing two types of tissue, a gel and two electrodes and FIG. 3B showing a conceptual drawing of an electrical field generated.

FIG. 3 show simulation result of tissue regions protection by means of non-conductive gel 6 used as a spacer (tissue 1 conductivity=tissue 5 conductivity=1 mS/cm, gel conductivity=0.1 mS/cm; gel region diameter=10 mm, gel region height=0.5 mm; tissue 1 thickness=1 mm; electrode diameter=0.1 mm, electrode separation distance=2 mm). In FIG. 3A this is shown a vertical plane that comprises both electrode axes. FIG. 3B shows a simulated image of a horizontal plane at the height denoted by gray line in left figure (~1/4 of tissue 1 thickness at region of interest). Black color indicates E<500 V/cm (no effect); hatch marks 500 V/cm E<1000 V/cm (reversible electroporation); and white E≧1000 V/cm (irreversible electroporation).

Electric Field Homogenization in Irregularly Shaped Tissues (3.1.2)

The example presented here is relevant to the application discussed in section 1.3. That is, the homogenization of the electric field in irregularly shaped tissues by means of matched conductivity additives.

Figure 4:
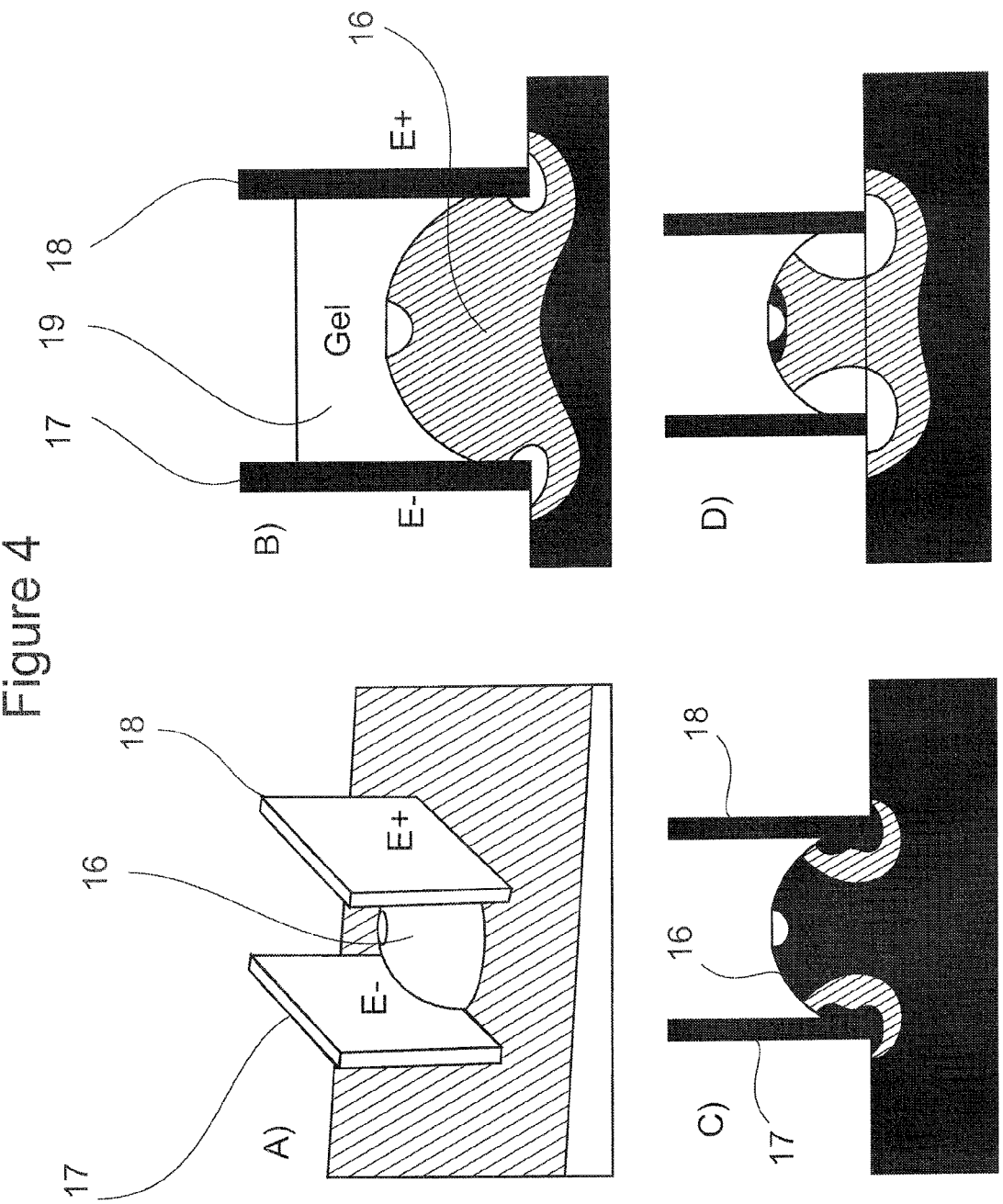
FIG. 4 includes 4A, 4B, 4C and 4D each of which show conceptual views of a simulation of electroporation being carried out between two electrodes with the conceptual model shown in FIG. 4A and FIG. 4B showing the electrical field magnitude resulting from simulation when gel is present, FIG. 4C showing a simulated electrical field magnitude when matched conductivity gel is not employed and FIG. 4D showing the results of FIG. 4C when the voltage provided by the electrodes is increased.

FIG. 4 shows a simulation of the electroporation of a semispherical tumor 16 (diameter=1 cm) at 550V. FIG. 4A shows a model employed in the simulation. FIG. 4B shows the resulting electric field magnitude from the simulation when gel 19 is present (vertical plane across the center of the electrodes). FIG. 4C shows a simulated electric field magnitude when matched conductivity gel is not employed (vertical plane across the center of the electrodes 17 and 18). FIG. 4D is the same as FIG. 4C but now voltage between electrodes is 1100V.

The structure depicted in FIG. 4A could correspond to the case of an irregularly shaped hard tumor electroporated through plate electrodes. The model consists of a semi-sphere (diameter=10 mm) on top of a square prism (50 mm×50 mm×20 mm) that represents the tissue (conductivity=1 mS/cm) and two plate electrodes (20 mm×10 mm×1 mm; conductivity=1000 S/cm) on two opposite sides of the semi-sphere. An extra irregularity in the shape of a semi-spherical depression (diameter=2 mm) has been included at the top of the tissue part. The number of elements of the mesh is 21,888. The voltage applied between electrodes is 550 V.

The simulation result of electroporation in the absence of a gel is shown in FIG. 4C. The electric field distribution is extremely heterogeneous. Furthermore, even in the case that very high voltages are employed (FIG. 4D), there are regions that are not electroporated. Of course, this is something not acceptable in cancer treatment and, maybe because of that, needle array electrodes are preferred for this kind of tumors rather than plate electrodes. On the other hand, when the addition of a matched conductivity gel is simulated (FIG. 4B) the results show that the electric field is much more homogeneous, even in this case in which the conductivity matching between tissue and gel conductivities is not perfect (matching error=30%).

Electric Field Homogenization in Tissues Containing Blood Vessels (3.1.3)

The simulation presented here is also related to section 1.3. The current case represents the reversible electroporation of a region that contains a blood vessel in its vicinity (FIG. 5A). The electroporation is performed with two parallel arrays of needle electrodes that should produce a quite homogeneous field within the region between them.

Figure 5:
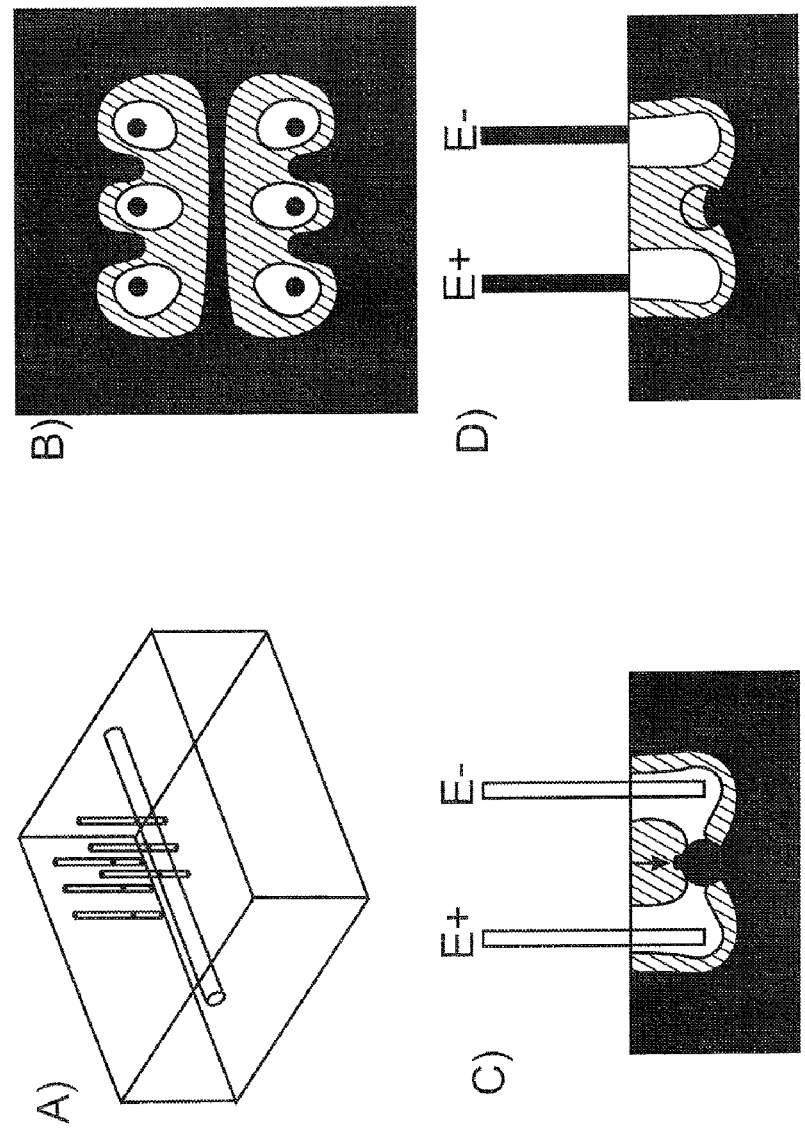
FIG. 5 includes FIG. 5A, 5B, 5C and 5D with FIG. 5A showing a conceptual perspective view of an electroporation system and FIG. 5B showing a conceptual view of a field generated by the six electrodes providing a particular field distribution.

FIG. 5 shows a simulation of the reversible electroporation of a square region that contains a blood vessel (diameter=3 mm) on its bottom boundary. FIG. 5A shows a model employed in the simulation, each electrode (E+ and E−) is constituted of an array of three needles (diameter=1 mm, separation=5 mm, penetration depth=5 mm); the separation distance between both arrays is 10 mm; blood vessel conductivity=10 mS/cm and tissue conductivity=1 mS/cm; applied voltage=1000 V. FIG. 5B shows a horizontal section of the simulated field magnitude at the top interface between the blood vessel and the parenchyma; white arrows indicate the region on top of the blood vessel that is not electroporated at all. FIG. 5C shows a vertical section, across the array centers, of the simulation results; the white arrow also indicates the region the on top of the blood vessel that is not electroporated at all. FIG. 5D show the same result when blood vessel conductivity is changed from 10 mS/cm to 1.5 mS/cm.

The model used for the simulation consists of: 1) a rectangular prism (50 mm×50 mm×20 mm) that represents the tissue an has a of conductivity 1 mS/cm; 2) a cylinder that represents the blood vessel (conductivity=10 mS/cm; diameter=3 mm, length=50 mm) that goes from one lateral side of the prism to the other at a depth of 5 mm; and 3) two electrode arrays placed in parallel at a distance of 10 mm between them. Each one of both arrays consists of three cylindrical rods (conductivity=1000 S/cm; diameter=1 mm, length=15 mm, separation distance=5 mm). The number of elements of the mesh is 68,571. The voltage applied between both arrays is 1000 V.

Simulation results show that a thin strip of tissue is not electroporated because of resulting field distribution heterogeneity (FIG. 5B and FIG. 5C). On the other hand, when blood is replaced by a matched conductivity additive (vessel conductivity changes from 10 mS/cm to 1.5 mS/cm), the simulated field distribution (FIG. 5D) is much more homogeneous and the objective of completely electroporating the region between electrodes is achieved.

Subdermal Electrodes (3.1.4)

The example presented here is relevant to the application discussed in section 1.4.1. That is, the use of injectable electrodes in order to protect specific tissue regions.

FIG. 6 shows a simulation of muscle (thickness=5 mm) electroporation at 700 V through injected semi-ellipsoidal gel regions connected to metallic needles with insulation on their shaft (E+ and E−). (a) Model employed in the simulation; gel conductivity=200 mS/cm, muscle conductivity=1 mS/cm, skin conductivity=0.1 mS/cm. FIG. 6B shows the resulting electric field magnitude from the simulation. The number of elements of the mesh is 196,534.

For the case shown in FIG. 6A, the objective is to reversibly electroporate the inner tissue (rectangular prism (20 mm×20 mm×5 mm); conductivity=1 mS/cm) without damaging the outer layers (mantle with thickness of 1 mm; conductivity=0.1 mS/cm). This may be considered a complimentary case to that presented in FIG. 2A. To perform such selective electroporation, the invention may use the injection of conductive gels at both sides of the region to be electroporated through needles with insulation on their shaft. With this method both regions will behave as parallel plate electrodes (gel regions are modeled here as half ellipsoid volumes (10 mm×10 mm×0.5 mm) with a conductivity of 200 mS/cm). Indeed, according to the simulation results (FIG. 6B) such behavior is obtained. Note, however, that enhancement of electric fields at gel region edges occurs and that causes in some damage to top tissues (skin).

Hollow Structure Electroporation (3.1.5)

This example shows a simulation of the case presented in FIG. 2B. An empty vessel is filled in its central region with a high conductivity gel. Then, electroporation voltage is applied between this gel and an external large electrode (FIG. 7A). If the voltage is properly selected, significant results in terms of selectivity of electroporation can be achieved. This is illustrated by the result of the simulation (FIG. 7B). The figure shows that only the vessel wall in contact with the gel is electroporated.

The model (FIG. 7A) consists of a large cylinder (diameter=100 mm, length=80 mm) that stands for the tissue between the cavity and the external electrode (conductivity=1000 S/cm); a cylindrical cavity (diameter=9 mm) with infinite resistivity; a thin (thickness=0.5 mm) wall between the cavity and the tissue with conductivity=0.25 mS/cm; and a cylinder (diameter=9 mm, length=20 mm) in the center of the geometry (not visible in FIG. 7A) that stands for the inner gel electrode and that has a conductivity of 200 mS/cm. The applied voltage between the internal electrode (inside the gel) and the external electrode is 200 V. The number of elements of the mesh is 56,364.

Figure 7:
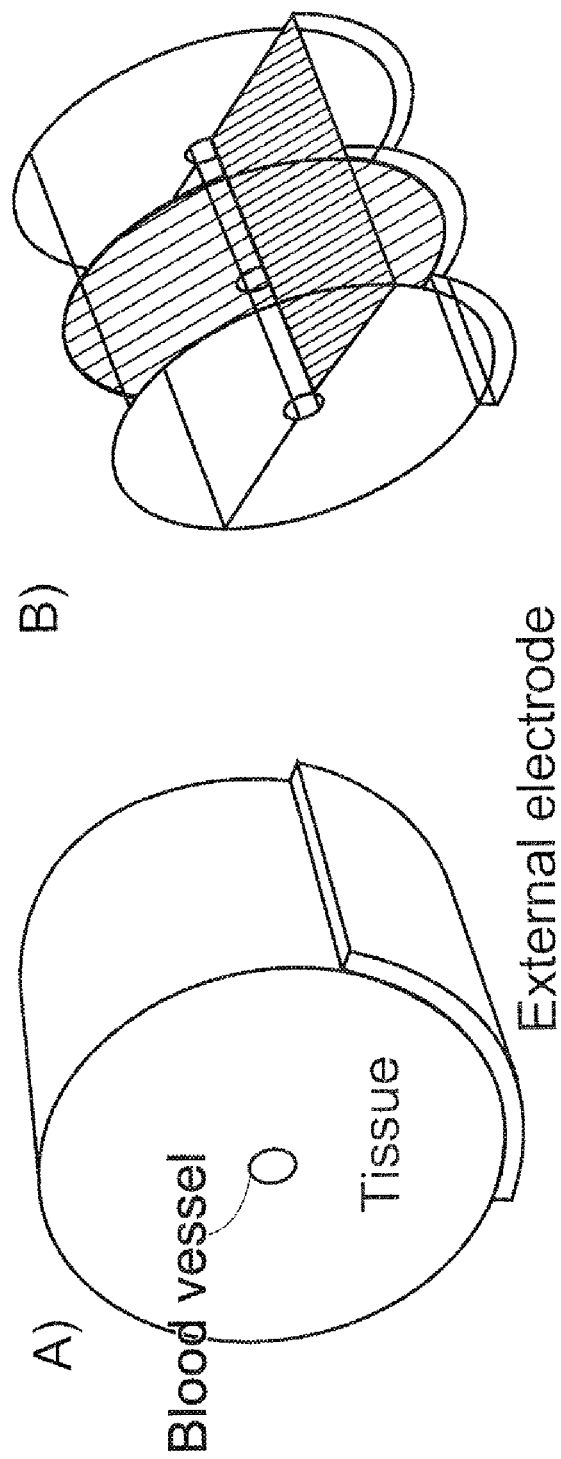
FIG. 7 includes 7A and 7B with FIG. 7A showing the external electrode around a blood vessel and FIG. 7B showing a conceptual positioning of components in the vessel such as a blood vessel.

FIG. 7 shows a simulation of empty blood vessel (outer diameter=10 mm, inner diameter=9 mm) electroporation at 200 V through an injected cylindrical gel region and an external metallic electrode. FIG. 7A shows the model employed in the simulation; gel cylinder is at the centre of the geometry, within the vessel; gel conductivity=200 mS/cm, tissue conductivity=1 mS/cm, vessel wall conductivity=0.25 mS/cm. FIG. 7B shows the resulting electric field magnitude from the simulation, two transverse cross sections at the center of the geometry are shown. Although it is difficult to appreciate, it can be observed that only the vessel walls at the location of the gel cylinder have been reversibly electroporated.

In Vivo Proof of Concept (3.2)

The results from the simulation of the structure resembling the in vivo proof of concept model (FIG. 8) show that if no gel had been applied the very tip of the lobe would have not electroporated at all (FIG. 9A). On the other hand, when the gel is applied, the effect of a matched conductivity gel (matching error=20%) is to cause complete irreversible electroporation of the whole lobe, including the tip (FIG. 9B). Macroscopic observation of the electroporated region (FIG. 10) before formaldehyde fixation agreed with the simulation result. Note that it is even possible to appreciate the concave shape of the irreversibly electroporated region that was predicted by the simulation. Microscopic observation (FIG. 11A) confirmed that entrapping of erythrocytes occurred through the whole lobe tip whereas it was not present in inner regions (FIG. 11B).

Figure 8:
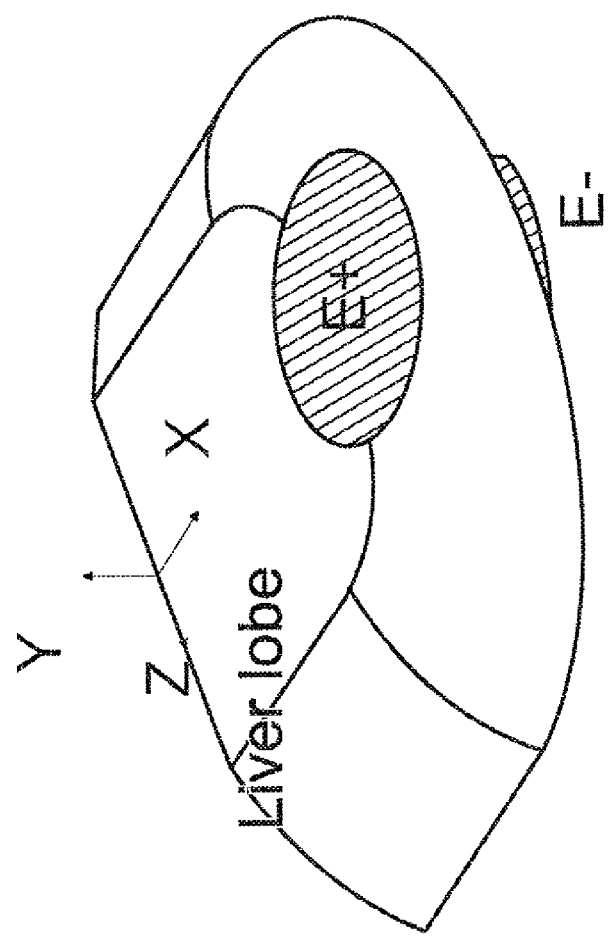
FIG. 8 is a conceptual perspective view of electrodes positioned relative to a portion of liver.

FIG. 8 shows a representation of the model employed to simulate the electroporation of the liver lobe tip (gel is not shown). The liver lobe tip is electroporated between the disk electrodes E+ and E− (diameter=10 mm, conductivity=1000 S/cm) separated at a distance of 5 mm. The applied voltage is 750 V and liver tissue conductivity is 1 mS/cm. The number of element of the mesh is 61,346.

Figure 9:
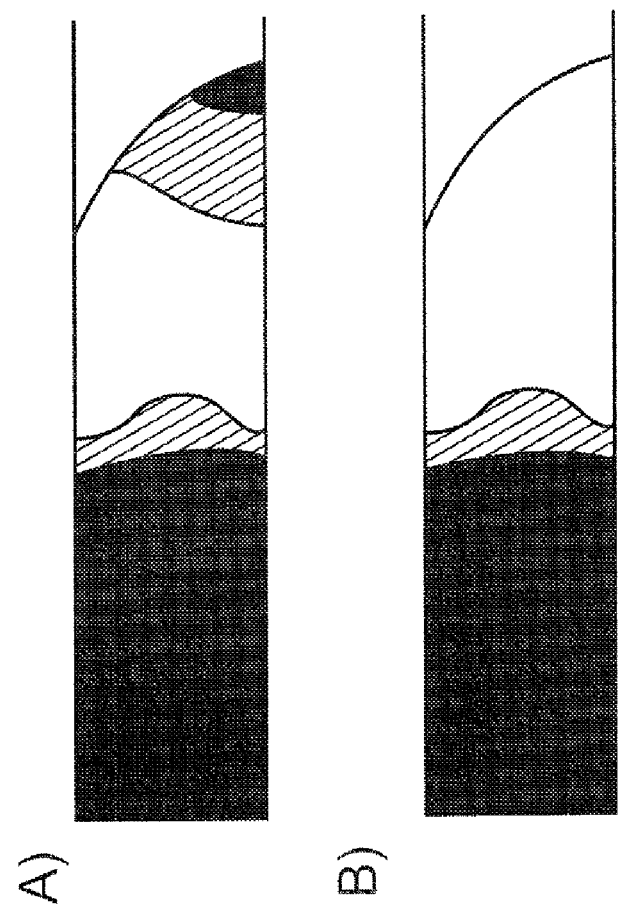
FIG. 9 includes FIGS. 9A and 9B showing conceptual views of electrical fields generated with FIG. 9A showing the field without the gel and FIG. 9B showing the field with the gel present.

FIG. 9 shows the results from the simulation of the liver lobe electroporation (plane x-y, z=0). FIG. 9A shows the simulated results without gel; an irregular electroporation pattern is obtained, a significant proportion of the tip is not irreversible electroporated. FIG. 9B shows simulated results of the presence of filling gel with conductivity=0.8 mS/cm is simulated; the tip region between the electrodes is irreversibly electroporated.

Figure 10:
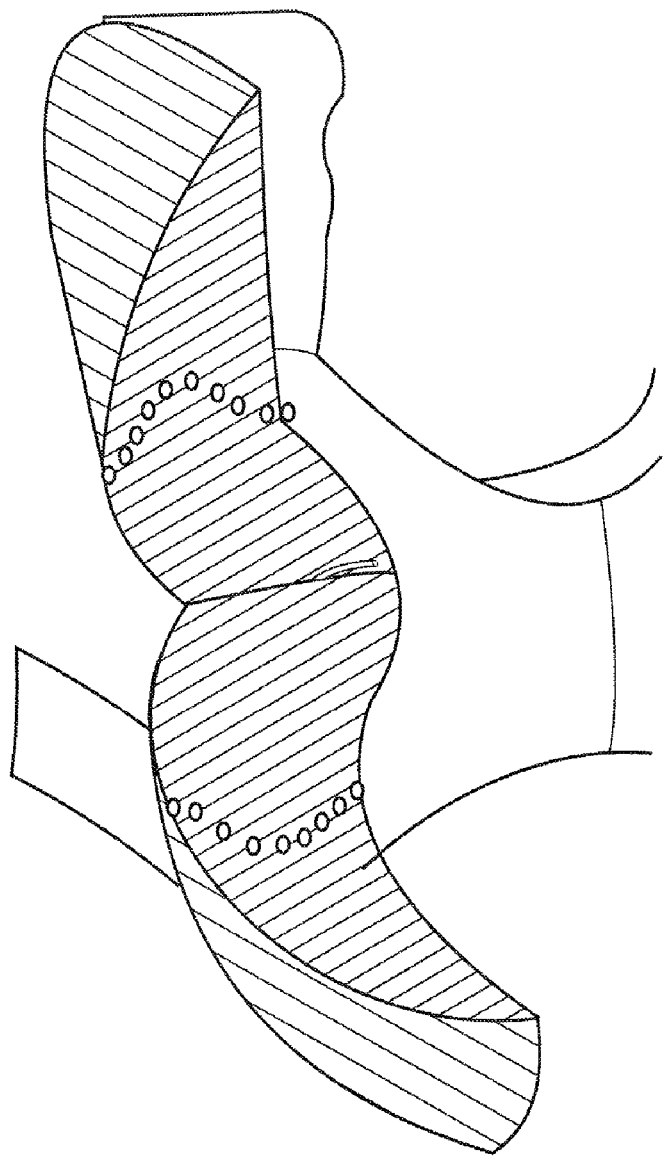
FIG. 10 is a picture of a rat liver lobe which has been subjected to electroporation.

FIG. 10 shows a picture of the electroporated rat liver lobe. It was cut and opened through the middle of the electroporated region. White dots are placed at the border between the treated tissue and the intact tissue.

Figure 11:
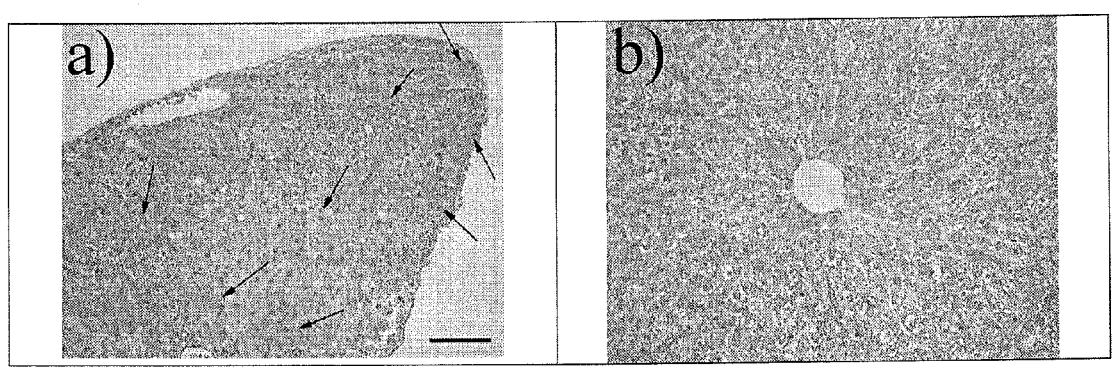

FIG. 11 shows a microscopic pictures of the electroporated liver lobe. FIG. 11A shows the tip of liver lobe; significant entrapping of erythrocytes (marked with arrows) denotes that irreversible electroporation has been produced. FIG. 11B shows the central vein area in an inner zone; no alteration can be observed. Bar indicates 100 µm, both pictures are at the same magnification.

Thermotherapy in Cavities and Vessels Based on Conductive Gels.

Among different applications, artificially induced hyperthermia is particularly useful as a local reinforcement process for chemotherapy and radiotherapy.

Currently, there exist some clinically available tools that can be employed to generate heat from the inside body vessels and cavities in a controlled fashion. However, all of these instruments employ some sort of cumbersome catheters that constrain their application in certain situations.

The present invention uses conductive gels for such a purpose. The method is equivalent to that one proposed for the electroporation of cavities. That is, to fill the cavity with a conductive gel and to apply an electric current between an electrode connected to that gel and an external electrode on the body surface. In this case, however, the applied electrical stimulus between both electrodes is not intended to perform cell membrane electroporation but to heat the tissue and/or the gel by means of the Joule effect. Therefore, the stimulus is an AC signal of lower amplitude but longer duration. As a matter of fact, the signal can be continuously injected through the treatment duration and the amplitude can be modulated according to some kind of temperature reading (e.g. temperature sensor on the catheter tip) in a controlled mode.

As with the electroporation described above, therapeutic agents, such as chemotherapeutic drugs, can be part of the gel composition.

Gel composition can be also differentiated for different purposes:

(1) In the case of high electrically conductive compositions (e.g high electrolytic content), few thermal losses due to Joule effect will be produced within the gel. Most energy will be dissipated in an annular region around the gel due to higher electric current density and higher resistance.

(2) In the case of moderate electrically conductive compositions, significant energy will be dissipated within the gel and surrounding tissues will be heated because direct contact with the heated gel rather than because direct Joule dissipation within them. This phenomenon can be enhanced by using additives, such as metal nano-particles, that increase the thermal conductivity of the gel.

With either thermotherapy or electroporation, DC voltages can be applied before, after or during (i.e. superimposed) the treatment between the electrodes in order to induce iontophoresis of drugs. This may be done to increase the penetration of these drugs into cells and tissues surrounding the gel.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of carrying out electroporation of tissue, comprising:
    inserting a gel into a patient by injection wherein the gel has a predetermined conductivity relative to surrounding tissue, the gel being semi-solid, elastic material comprised of matter in a colloidal state;
    applying current across tissue in an amount so that cells of the tissue are subjected to electroporation;
    wherein the conductivity of the gel is sufficiently below that of the surrounding tissue such that when current is applied substantially no current flows through the gel and the current is directed to a specific targeted area of tissue to be electroporated.

2. The method of claim 1, wherein the gel is comprised of a therapeutically active drug.

3. The method of claim 1, wherein the gel is a hydrogel comprised of water and solid phase polymer chains.

4. The method of claim 1, wherein the conductivity of the gel is adjusted by incorporating a predetermined concentration of ions in the gel.

5. The method of claim 4, wherein ions are derived from NaCl in the gel.

6. The method of claim 1 wherein the electroporation is reversible.

7. A method of carrying out electroporation of tissue, comprising:
    inserting a gel into a patient by injection wherein the gel has a predetermined conductivity relative to surrounding tissue the gel being semi-solid, elastic material comprised of matter in a colloidal state;
    applying current across tissue in an amount so that cells of the tissue are subjected to electroporation:
    wherein the conductivity of the gel is substantially the same as that of surrounding tissue and when current is applied a homogeneous electrical field is applied and a specific area of targeted tissue is electroporated.

8. A method of carrying out electroporation of tissue, comprising:
    inserting a gel into tissue in a patient by injection wherein the gel has a predetermined conductivity relative to tissue surrounding the gel, wherein the gel is a semi-solid, elastic material comprised of matter in a colloidal state;
    applying current across tissue in an amount so that cells of the tissue are subjected to electroporation;
    wherein the conductivity of the gel is predetermined by incorporating a known concentration of ions in the gel.

9. The method of claim 8, wherein the ions are derived from NaCl dissolved in the gel and wherein the conductivity of the gel is sufficiently below that of the surrounding tissue such that when current is applied substantially no current flows through the gel and the current is directed to a specific targeted area of tissue to be electroporated.

10. The method of claim 8, wherein the gel is a hydrogel comprised of water and solid phase polymer chains and wherein the conductivity of the gel is substantially the same as that of surrounding tissue and when current is applied a homogeneous electrical field is applied and a specific area of targeted tissue is electroporated.

11. The method of claim 8, wherein the gel is comprised of a therapeutically active drug.

12. The method of claim 8, wherein the electroporation is reversible.

13. A method of carrying out irreversible electroporation of tissue, comprising:
    inserting a gel into a patient by injection wherein the gel has a predetermined conductivity relative to surrounding tissue the gel being semi-solid, elastic material comprised of matter in a colloidal state;
    applying current across tissue in an amount so that cells of the tissue are subjected to irreversible electroporation;
    wherein the conductivity of the gel is sufficiently below that of the surrounding tissue such that when current is applied substantially no current flows through the gel and the current is directed to a specific targeted area of tissue to be irreversibly electroporated.

14. The method of claim 13, wherein the gel is comprised of a therapeutically active drug.

15. The method of claim 13, wherein the gel is a hydrogel comprised of water and solid phase polymer chains.

16. The method of claim 13, wherein the conductivity of the gel is adjusted by incorporating a predetermined concentration of ions in the gel.

17. The method of claim 16, wherein ions are derived from NaCl in the gel.

18. A method of carrying out irreversible electroporation of tissue, comprising:
    inserting a gel into a patient by injection wherein the gel has a predetermined conductivity relative to surrounding tissue the gel being semi-solid, elastic material comprised of matter in a colloidal state;
    applying current across tissue in an amount so that cells of the tissue are subjected to irreversible electroporation;
    wherein the conductivity of the gel is substantially the same as that of surrounding tissue and when current is applied a homogeneous electrical field is applied and a specific area of targeted tissue is irreversibly electroporated.

19. A method of carrying out irreversible electroporation of tissue, comprising:
    inserting a gel into tissue in a patient by injection wherein the gel has a predetermined conductivity relative to tissue surrounding the gel, wherein the gel is a semi-solid, elastic material comprised of matter in a colloidal state;

applying current across tissue in an amount so that cells of the tissue are subjected to irreversible electroporation;

wherein the conductivity of the gel is predetermined by incorporating a known concentration of ions in the gel.

20. The method of claim 19, wherein the ions are derived from NaCl dissolved in the gel and wherein the conductivity of the gel is sufficiently below that of the surrounding tissue such that when current is applied substantially no current flows through the gel and the current is directed to a specific targeted area of tissue to be irreversibly electroporated.

21. The method of claim 19, wherein the gel is a hydrogel comprised of water and solid phase polymer chains and wherein the conductivity of the gel is substantially the same as that of surrounding tissue and when current is applied a homogeneous electrical field is applied and a specific area of targeted tissue is irreversibly electroporated.

22. The method of claim 19, wherein the gel is comprised of a therapeutically active drug.

* * * * *